United States Patent
Schattauer et al.

(10) Patent No.: US 6,510,358 B1
(45) Date of Patent: Jan. 21, 2003

(54) IMPREGNATION PROCESS AND DEVICE FOR MONITORING THE IMPREGNATION OF A CARRIER MATERIAL

(75) Inventors: Dora Schattauer, Oberhausen (DE); Franz-Josef Pfreundt, Stelzenberg (DE); Aivars Zemitis, Kaiserslautern (DE); Kai Velten, Kaiserslautern (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/549,274

(22) Filed: Apr. 14, 2000

Related U.S. Application Data

(63) Continuation of application No. PCT/DE98/02925, filed on Oct. 1, 1998.

(30) Foreign Application Priority Data

Oct. 14, 1997 (DE) ......................... 197 45 406

(51) Int. Cl.⁷ ............................ G06F 19/00; G01N 27/22
(52) U.S. Cl. ........................ 700/117; 324/545; 324/772; 702/166; 73/304 C; 700/265; 700/110
(58) Field of Search ..................... 700/117, 108–110, 700/265, 266; 702/166, 170; 324/545, 689, 772; 340/648; 427/8, 9, 10; 29/605; 73/304 C

(56) References Cited

U.S. PATENT DOCUMENTS

| | | | |
|---|---|---|---|
| 3,866,316 A | * 2/1975 | Takechi et al. | 29/605 |
| 4,187,327 A | * 2/1980 | Lapp et al. | 427/8 |
| 4,856,320 A | 8/1989 | Bose et al. | 73/30 |
| 4,907,442 A | 3/1990 | Jones et al. | 73/38 |
| 4,994,751 A | 2/1991 | Cook et al. | 324/674 |
| 5,682,102 A | * 10/1997 | Takahashi et al. | 324/545 |

FOREIGN PATENT DOCUMENTS

| | | |
|---|---|---|
| DE | 26 09 869 A1 | 9/1977 |
| DE | 36 17 598 A1 | 11/1987 |
| DE | 44 46 597 A1 | 6/1996 |
| DE | 195 36 766 A1 | 4/1997 |
| JP | 01057163 | * 3/1989 |

OTHER PUBLICATIONS

Zhong Cai: "Analysis of Mold Filling in RTM Process", Journal of COMPOSITE MATERIALS, vol. 26, No. 9, 1992, pp. 1310–1338.

* cited by examiner

Primary Examiner—Leo Picard
Assistant Examiner—Steven R. Garland
(74) Attorney, Agent, or Firm—Laurence A. Greenberg; Werner H. Stemer; Ralph E. Locher

(57) ABSTRACT

An impregnation process in which a carrier material is impregnated by an impregnation medium. The impregnation of the carrier material is determined via a dielectric constant of the carrier material, preferably by a determination of a capacitance. A device for monitoring the impregnation of the carrier material with the impregnation medium is also disclosed.

18 Claims, 2 Drawing Sheets

IMPREGNATION PROCESS AND DEVICE FOR MONITORING THE IMPREGNATION OF A CARRIER MATERIAL

CROSS-REFERENCE TO RELATED APPLICATION

This is a continuation of copending International Application PCT/DE98/02925, filed Oct. 1, 1998, which designated the United States.

BACKGROUND OF THE INVENTION

Field of the Invention

The invention relates to an impregnation process, in which a carrier material is impregnated with an impregnation medium. The invention further relates to a device for monitoring the impregnation of a carrier material with an impregnation medium.

The article titled "Analysis of Mold Filling in RTM Process" by Zhong Cai in the Journal of Composite Materials, Vol. 26, 9/1992 discloses an impregnation process. A resin transfer molding (RTM) process is described, in which fibers are impregnated by a resin to form a composite material. A numerical model is presented, which is based on Darcy's law and describes the impregnation process.

SUMMARY OF THE INVENTION

It is accordingly an object of the invention to provide an impregnation process and a device for monitoring the impregnation of a carrier material, which overcome the above-mentioned disadvantages of the prior art devices and methods of this general type.

With the foregoing and other objects in view there is provided, in accordance with the invention, an impregnation process, which comprises:

impregnating a carrier material with an impregnation medium, so that a dielectric constant of the carrier material changes;

measuring a measured variable dependent upon the dielectric constant; and determining a functional interrelationship between a reference impregnation and the measured variable and drawing a conclusion from the functional interrelationship as to an impregnation of the carrier material, the functional interrelationship being determined with reference to the steps of:

defining a degree of the impregnation as a ratio of an impregnated to-an unimpregnated volume of the carrier material;

setting up a sequence of degrees of the impregnation with predetermined process parameters, and allocating the reference impregnation with a spatial distribution in the carrier material of at least one unimpregnated dry region and at least one impregnated moist region to each of the degrees of the impregnation by using a simulation with reference to a flow model;

allocating a first dielectric constant to the at least one unimpregnated dry region and allocating a second dielectric constant to the at least one impregnated moist region; and allocating the measured variable to the reference impregnation with the aid of the first dielectric constant and the second dielectric constant, and thus obtaining the functional interrelationship.

The object directed at specifying an impregnation process is achieved, according to the invention, by an impregnation process in which the carrier material is impregnated with the impregnation medium, so that the dielectric constant of the carrier material changes. The measured variable dependent upon the dielectric constant is measured and the impregnation of the carrier material being determined therefrom.

The invention is based on the finding that the dielectric constant of the carrier material is changed by the penetration of the impregnation medium into the carrier material. Via the determination of the dielectric constant it is possible, for example, to conclude how far the carrier material has been impregnated by the impregnation medium. Thus, it is possible to monitor the impregnation process.

The measured variable that is preferably used is the electrical capacitance of a configuration of electrical conductors, in which configuration the carrier material serves as the dielectric. The configuration in the form of a capacitor enables a simple determination of the dielectric constant via the measurement of an electrical capacitance. The capacitance can, for example, be determined by application of a direct voltage, or alternatively via the determination of a capacitive resistance.

Preferably, a temporal progression of the measured variable is measured and a temporal progression of the impregnation is determined therefrom. On this bases, it is possible to represent the temporal progression of variables characterizing the impregnation process.

Further preferably, a functional interrelationship between a reference impregnation and the measured variable is determined, and a conclusion is drawn from the functional interrelationship concerning the impregnation. The determination of a reference impregnation as a function of the measured variable represents one possibility for obtaining, from the measured variable, a value for the impregnation.

Preferably, the temporal progression of the impregnation is computed in accordance with the interrelationship $D(t)=D_R(C(t))$ where D is the impregnation, $D_R$ a reference impregnation, C the measured variable, in particular the capacitance, and t the time. Using the resulting functional interrelationship of the reference impregnation with the measured variable, the temporal progression of the impregnation may be obtained directly through the measured temporal progression of the measured variable with the aid of the above-mentioned interrelationship.

Preferably, the functional interrelationship is determined in that a degree of impregnation is defined as the ratio of the impregnated to the unimpregnated volume of the carrier material. For a sequence of degrees of impregnation with predetermined process parameters, the reference impregnation with a spatial distribution in the carrier material of at least one unimpregnated dry region and at least one impregnated moist region is allocated to each degree of impregnation by use of a simulation with reference to a flow model. A first dielectric constant is allocated to the at least one dry region and a second dielectric constant is allocated to the at least one moist region. A measured variable is allocated to each reference impregnation with the aid of these dielectric constants, and thus the functional interrelationship which is sought is obtained.

The impregnation medium penetrates into the carrier material with the formation of a flow front. In this case, dry regions and/or moist regions may cohere in such a way that they represent in each case one cohesive volume. However, the flow front can also lead to a complex spatial distribution of dry regions and moist regions. Through differing dielectric constants of these regions, results in a complex electric field. By use of the mentioned mode of procedure, it is now possible, even in the case of flow fronts of the impregnation medium in the carrier material which are of more complicated form, to produce a functional interrelationship between an impregnation and the capacitance. This takes place by use of a simulation which is based on a flow model and which delivers, for a predetermined percentage impregnation, a specified distribution of dry regions and moist regions. In that in each instance a specified dielectric constant is allocated to these different regions, it is possible to compute a potential distribution in the carrier material, in dependence upon the spatial distribution of these different regions which becomes apparent. The capacitance is then obtained from the formula $$C = \frac{1}{U} \int_\Gamma \varepsilon_0 \varepsilon_r \nabla \varphi \cdot n \, ds$$

In this case, the integration is carried out over an area $\Gamma$ of electrodes of the conductor configuration which are employed for the capacitance measurement. $\varepsilon_0$ is the dielectric constant of a vacuum, $\varepsilon_r$ a mean dielectric constant that is obtained from the dielectric constants of the dry regions and the moist regions, $\varphi$ is a potential and U a voltage applied to the electrodes.

Further preferably, for a porous carrier material the spatial distribution of the reference impregnation is computed using Darcy's law for a flow of a Newtonian impregnation medium or using a suitable modification of Darcy's law for a flow of a non-Newtonian impregnation medium. For porous media, the computation of the propagation of flow fronts may be simulated with the aid of Darcy's law, which, as is acknowledged, sufficiently well reproduces the physical conditions.

Preferably, a penetration depth of the impregnation medium into the carrier material is obtained from the impregnation. Further preferably, a temporal progression of the penetration depth is obtained and at least one of the following variables of the carrier material is determined therefrom:

a filtration coefficient, a flow resistance, a permeability, and a relative porosity.

In the case where the impregnation medium flows with a straight flow front through a mold of constant diameter, the following interrelationships apply:

$$q_0(t) = \frac{d}{dt} E(t) \tag{1}$$

$$K(E(t)) = \frac{q_0(t)\mu}{\Phi^2 \frac{d}{dt}\left(\frac{\Delta p(t)}{q_0(t)}\right)} \tag{2}$$

$$\mu(E(t)) = \frac{\frac{d}{dt}\left(\frac{\Delta p(t)}{q_0(t)}\right) K \Phi^2}{q_0} \tag{3}$$

$$\Phi(E(t)) = \sqrt{\frac{q_0(t)\mu}{K \frac{d}{dt}\left(\frac{\Delta p(t)}{q_0(t)}\right)}} \tag{4}$$

-continued $$\frac{K \Phi^2}{\mu}(E(t)) = \frac{q_0}{\frac{d}{dt}\left(\frac{\Delta p(t)}{q_0(t)}\right)} \tag{5}$$

The symbols that are used are explained in the table below:

| Symbol | Meaning | Unit |
| --- | --- | --- |
| $E(t)$ | Penetration depth as a function of time | m |
| $K$ | Permeability | $m^2$ |
| $\Phi$ | Relative porosity | |
| $\mu$ | Viscosity | Pa × s |
| $\frac{K\Phi^2}{\mu}$ | Conductivity | $\frac{m^2}{Pa \cdot s}$ |
| $\frac{\mu}{K\Phi^2}$ | Flow resistance | $\frac{Pa \cdot s}{m^2}$ |
| $q_0$ | Flow rate | $\frac{m}{s}$ |
| $\Delta_p$ | Pressure difference | Pa |

For simple geometries of the carrier material, e.g. a cylinder, a simple and uniform flow front results. In this case, an impregnation and thus a penetration depth of the impregnation medium with time may be derived from the determination of the measured variable, without computing a reference impregnation. Via the determination of such a temporal progression of the penetration depth, it is then again possible to obtain a material property such as the filtration coefficient of the flow resistance. Further preferably, a temporal progression of the penetration depth is obtained, and a viscosity of the impregnation medium is obtained therefrom.

Preferably, a resin, in particular an epoxy resin, is used as the impregnation medium. Impregnations with resins and in particular with epoxy resins play a major part, for example, in the manufacture of composite materials and in the impregnation of electric windings of generators. Preferably, the fibers of a fiber composite material to be manufactured are used as the carrier material.

Preferably, an electrical insulating material is used as the carrier material. Further preferably, the electrical winding of a stator of a generator, in particular of a turbogenerator, is impregnated, in particular in a total impregnation process (VPI process, VPI=Vacuum Pressure Impregnation). Nowadays, turbogenerators are in many cases manufactured via a total impregnation of their stator. In this case, the stator is flooded with epoxy resin and impregnated by the epoxy resin under pressure and at high temperature. Following completion of curing of the epoxy resin, the result is accordingly a particularly durable and resistant stator cladding.

Preferably, from the measured impregnation a conclusion is drawn as to the presence of an impregnation defect in the carrier material. Impregnation defects are permanently unimpregnated regions. The measurement of the impregnation with the aid of the measured variable makes it possible, for example, to detect impregnation defects occurring by reason of material properties. An indication of an impregnation defect may in particular be that the customary final capacitance, i.e. the capacitance that customarily becomes apparent at the end of the impregnation process, is not attained.

According to the invention, the object directed at specifying a device is achieved by a device for monitoring the impregnation of the carrier material with the impregnation medium, in which a conductor configuration is disposed in such a way that the carrier material serves as a dielectric influencing the capacitance of the conductor configuration and in which a measuring device for measuring the electrical capacitance is connected to the conductor configuration.

The advantages of such a device are obtained in a manner corresponding to the above statements concerning the advantages of the impregnation process.

Preferably, the carrier material is an insulation of a conductor rod of the stator of the turbogenerator. In this case, the conductor configuration is an electrically conductive strip that surrounds the insulation and embraces the electrical conductor of the conductor rod. The impregnation during a total impregnation process of the stator of the turbogenerator may be monitored in a particularly simple manner by this configuration. It is merely necessary to measure the capacitance between the electrically conductive strip and the electrical conductor of the conductor rod. Via the capacitance measurement, it is possible to draw a conclusion as to the impregnation in accordance with the above statements concerning the impregnation process.

Other features which are considered as characteristic for the invention are set forth in the appended claims.

Although the invention is illustrated and described herein as embodied in an impregnation process and a device for monitoring the impregnation of a carrier material, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE PREFERRED EMBODIMENTS

Figure 1:
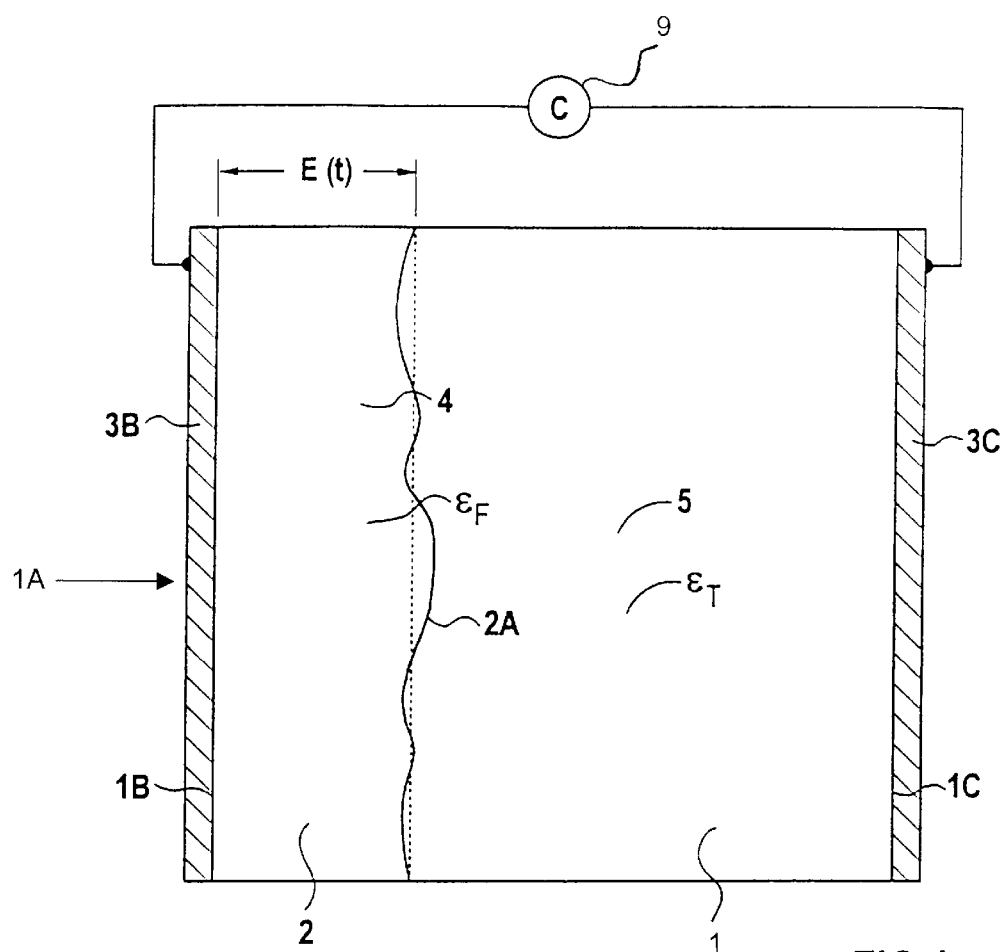
FIG. 1 is a diagrammatic, sectional view of a body to be impregnated.

In all the figures of the drawing, sub-features and integral parts that correspond to one another bear the same reference symbol in each case. Referring now to the figures of the drawing in detail and first, particularly, to FIG. 1 thereof, there is shown a longitudinal cross section through a rectangular body 1A made from a carrier material 1. An electrical conductor configuration 3 is disposed at narrow sides 1B, 1C of the body 1A. The configuration 3 contains a first conductor 3B on the narrow side 1B and a second conductor 3C on the narrow side 1C. The conductors 3B and 3C are connected to a measuring device 9 in such a way that a capacitance of the conductor configuration 3 can be determined by the measuring device 9. The carrier material 1 is impregnated with an impregnation medium 2, commencing from the narrow side 1B. The impregnation medium 2 penetrates the carrier material 1 over a course of time, from the narrow side 1B to the narrow side 1C. In this case, a flow front 2A is formed. The flow front 2A subdivides the carrier material 1 into a moist region 4 and a dry region 5. The moist region 4 has a dielectric constant $\in_F$. The dry region 5 has a dielectric constant $\in_T$. The flow front 2A defines a mean penetration depth E(t) of the impregnation medium 2 into the carrier material 1 at a specified time t.

Figure 2:
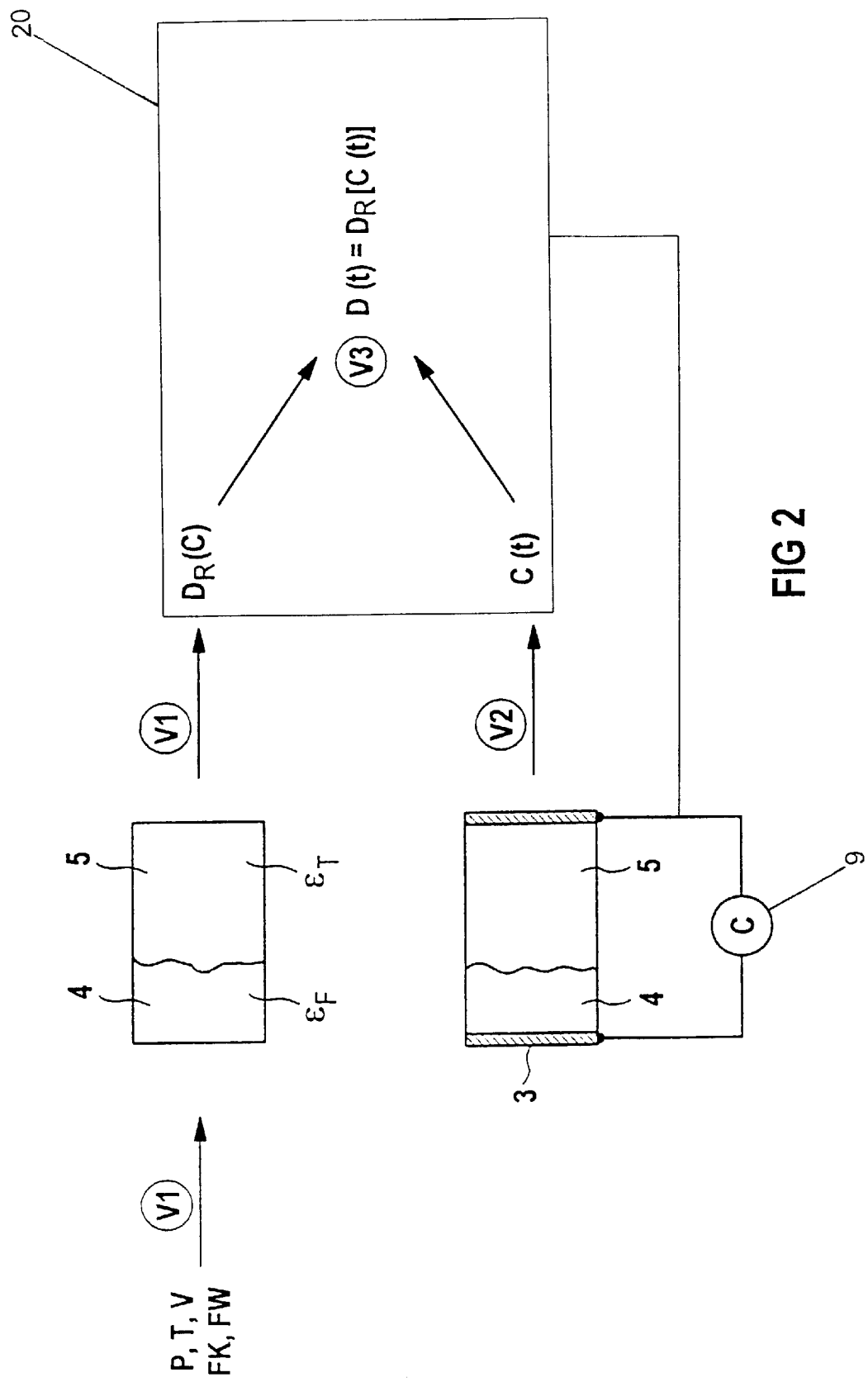
FIG. 2 is a representation of process steps for computing the impregnation from a capacitance according to the invention.

How the impregnation of the carrier material 1 is obtained from a capacitance measurement is explained in the text that follows in FIG. 2. Three process steps V1, V2, V3 are represented in FIG. 2. In the process step V1, a functional interrelationship D(C) between a reference impregnation $D_R$ and the capacitance C is computed in a process device 20. To this end, use is made of process parameters. The processing device 20 can be part of the measuring device 9 or a separate device communicating with the measuring device 9.

A pressure P under which the impregnation medium 2 is pressed into the carrier material 1, a prevailing temperature T, a viscosity V of the impregnation medium 2 and a filtration coefficient FK or a flow resistance FW of the carrier material 1, leading to a permeability S of the carrier material 1. For a porous carrier material 1, a determination is made, with the aid of the Darcy equation, as to what spatial distribution of the impregnated moist region 4 and the unimpregnated dry region 5 is to be expected for a predetermined degree of impregnation. In a one-dimensional form, the Darcy equation is written as:

$$q = \frac{S}{V} \frac{\delta p}{\delta x}$$

where q is a flow rate of the impregnation medium 2, S is a permeability of the carrier material 1, V is the viscosity of the impregnation medium 2 and $\delta p/\delta x$ is a pressure gradient. From the thus simulated spatial distribution of the moist region 4 and the dry region 5, it is possible to obtain the capacitance C in that the dielectric constant $\in_F$ is assigned to the moist region 4 and the dielectric constant $\in_T$ is assigned to the dry region 5. In this way, the desired functional interrelationship $D_R(C)$ between the reference impregnation $D_R$ and the capacitance C is established in the processing device 20 used for determining and storing the simulation results.

In a second process step V2, the capacitance C is measured with the aid of the measuring device 9 in accordance with FIG. 1, as a function of time t. The results of the process steps V1 and V2 are combined in a process step V3, in which the impregnation D is determined as a function of time t from the formula $D(t)=D_R(C(t))$.

Depending upon the desired accuracy of the measurement, the form of the flow fronts 2A and thus the precise spatial distribution of the moist region 4 and the dry region 5 may be negligible. In this case, a simulation using a flow model, for example using the Darcy equation, is not necessary. A direct conclusion can then be drawn from the capacitance as to a percentage proportion of the moist region 4 and the dry region 5, i.e. as to the impregnation D.

Figure 3:
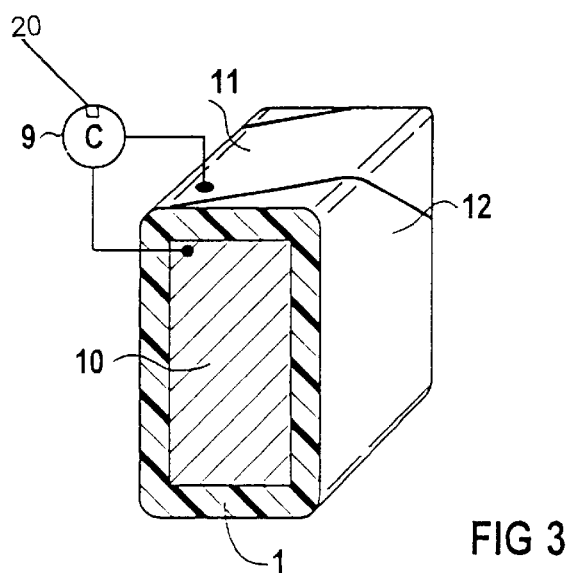
FIG. 3 is a sectional view of a conductor rod of a stator of a turbogenerator.

FIG. 3 shows a section of a conductor rod 12 of a stator of a turbogenerator. The conductor rod 12 consists of an electrical conductor 10, preferably of copper. It is surrounded by an insulation 1, which in this case represents the carrier material 1. The insulation 1 is surrounded by an externally coiled protective glow strip, which is not shown in greater detail. A conductive strip 11 is wound over the protective glow strip. The conductive strip 11 and the conductor 10 are connected to the measuring device 9 for measuring the capacitance C received by the processing device 20. Such a conductor rod 12 is inserted into grooves of a package of metal sheets (not shown), and connected to other, correspondingly disposed conductor rods 12, to form an electrical winding. The entire configuration forms the stator of the turbogenerator. It is impregnated with an epoxy resin in a total impregnation process. To this end, the entire stator is introduced into a pressurized container. Under high temperature and high pressure, the epoxy resin, which forms the impregnation medium 2, is then introduced into the carrier material 1, i.e. the insulation 1. A perfect impregnation that has virtually no residues is essential for the purposes of the operational reliability and the service life of the generator. In that the capacitance C is measured with the aid of the measuring device 9, the impregnation of the insulation 1 can be monitored. By way of example, impregnation defects, i.e. unimpregnated regions can be detected, at the end of the impregnation process, in that a final capacitance that is obtained in the normal case is not pertained.

In addition to the application for the monitoring of the impregnation process in processes for the total impregnation of the stator, the invention can however also be advantageously employed in other areas. In particular, the manufacture of fiber composite materials frequently demands an impregnation with a resin. In this instance, monitoring of the impregnation process offers great advantages with respect to quality assurance.

We claim:

1. An impregnation process, which comprises:
   impregnating a carrier material with an impregnation medium, so that a dielectric constant of the carrier material changes;
   measuring a measured variable dependent upon the dielectric constant; and
   determining a functional interrelationship between a reference impregnation and the measured variable and drawing a conclusion from the functional interrelationship as to an impregnation of the carrier material, the functional interrelationship being determined with reference to the steps of:
      defining a degree of the impregnation as a ratio of an impregnated to an unimpregnated volume of the carrier material;
      setting up a sequence of degrees of the impregnation with predetermined process parameters, and allocating the reference impregnation with a spatial distribution in the carrier material of at least one unimpregnated dry region and at least one impregnated moist region to each of the degrees of the impregnation by using a simulation with reference to a flow model;
      allocating a first dielectric constant to the at least one unimpregnated dry region and allocating a second dielectric constant to the at least one impregnated moist region; and
      allocating the measured variable to the reference impregnation with the aid of the first dielectric constant and the second dielectric constant, and thus obtaining the functional interrelationship.

2. The impregnation process according to claim 1, which comprises using an electrical capacitance of a configuration of electrical conductors in which the carrier material serves as a dielectric, as the measured variable.

3. The impregnation process according to claim 1, which comprises measuring a temporal progression of the measured variable, and determining a temporal progression of the impregnation from the temporal progression of the measured variable.

4. The impregnation process according to claim 3, which comprises computing the temporal progression of the impregnation according to an interrelationship defined by:
$D(t)=D_R(C(t))$ where
   D is the impregnation,
   $D_R$ is the reference impregnation,
   C is the measured variable, and
   t is time.

5. The impregnation process according to claim 4, which comprises computing, for a porous carrier material, the spatial distribution of the reference impregnation using one of Darcy's law for a flow of a Newtonian impregnation medium and a suitable modification of Darcy's law for a flow of a non-Newtonian impregnation medium.

6. The impregnation process according to claim 4, which comprises defining the measured variable to be a measured capacitance.

7. The impregnation process according to claim 1, which comprises drawing a conclusion from the impregnation as to a presence of an impregnation defect in the carrier material.

8. An impregnation process, which comprises:
   impregnating a carrier material with an impregnation medium, such that a dielectric constant of the carrier material changes;
   measuring a measured variable dependent upon the dielectric constant;
   measuring a temporal progression of the measured variable and determining a temporal progression of the impregnation from the temporal progression of the measured variable;
   determining an impregnation of the carrier material from the measured variable; and
   obtaining a penetration depth of the impregnation medium into the carrier material from the impregnation.

9. The impregnation process according to claim 8, which comprises using an electric capacitance of a configuration of electric conductors in which the carrier material serves as a dielectric, as the measured variable.

10. The impregnation process according to claim 8, which comprises determining a temporal progression of the penetration depth, and determining at least one of a filtration coefficient, a flow resistance, a permeability, and a relative porosity of the carrier material from the temporal progression of the penetration depth.

11. The impregnation process according to claim 8, which comprises determining a temporal progression of the penetration depth, and obtaining a viscosity of the impregnation medium from the temporal progression of the penetration depth.

12. The impregnation process according to claim 8, which comprises using a resin, including an epoxy resin, as the impregnation medium.

13. The impregnation process according to claim 8, which comprises using fibers as the carrier material, and the fibers are impregnated for forming a fiber composite material to be used in manufacturing.

14. The impregnation process according to claim 8, which comprises using an electrical insulating material as the carrier material.

15. The impregnation process according to claim 14, which comprises impregnating an electrical winding of a stator of a generator, including a turbogenerator.

16. The impregnation process according to claim 15, which comprises performing a total impregnation process of the electrical winding of the stator of the generator.

17. A device for monitoring an impregnation of a carrier material with an impregnation medium, the carrier material being an insulation of a conductor rod of a stator of a turbogenerator, the conductor rod formed of a conductor configuration including an electrically conductive strip surrounding the carrier material and an electric conductor, the conductor configuration disposed such that the carrier material serves as a dielectric influencing a capacitance of the conductor configuration, the device comprising:

a measuring device to be connected to the conductor configuration for measuring the capacitance of the conductor configuration and outputting a measured variable, said measuring device having a processing device receiving the measured variable and determining a functional interrelationship between a reference impregnation stored in said processing device and the measured variable and drawing a conclusion from the functional interrelationship as to the impregnation of the carrier material, said processing device programmed to determine the functional interrelationship with reference to the steps of:

defining a degree of the impregnation as a ratio of an impregnated to an unimpregnated volume of the carrier material;

setting up a sequence of degrees of the impregnation with predetermined process parameters, and allocating the reference impregnation with a spatial distribution in the carrier material of at least one unimpregnated dry region and at least one impregnated moist region to each of the degrees of the impregnation by using a simulation with reference to a flow model;

allocating a first dielectric constant to the at least one unimpregnated dry region and allocating a second dielectric constant to the at least one impregnated moist region; and allocating the measured variable to the reference impregnation with the aid of the first dielectric constant and the second dielectric constant, and thus obtaining the functional interrelationship.

18. An impregnation process, which comprises:

impregnating a carrier material with an impregnation medium, such that a dielectric constant of the carrier material changes;

measuring a measured variable dependent upon the dielectric constant;

determining an impregnation of the carrier material from the measured variable;

obtaining a penetration depth of the impregnation medium into the carrier material from the impregnation; and determining a temporal progression of the penetration depth, and determining at least one of a filtration coefficient, a flow resistance, a permeability, and a relative porosity of the carrier material from the temporal progression of the penetration depth.

* * * * *